(12) United States Patent
Garland et al.

(10) Patent No.: US 6,205,198 B1
(45) Date of Patent: Mar. 20, 2001

(54) EXPOSURE COMPENSATION FOR DIGITAL RADIOGRAPHY SYSTEMS USING SPATIAL LOOK-UP TABLES

(75) Inventors: Harry T. Garland, Los Altos Hills; Gerald A. May, Saratoga, both of CA (US)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/154,179

(22) Filed: Sep. 16, 1998

(51) Int. Cl.[7] .................................................. H05G 1/64
(52) U.S. Cl. .................................. 378/98.7; 378/98.8
(58) Field of Search ............................. 378/98.7, 98.8; 382/132, 274, 275, 305

(56) References Cited

U.S. PATENT DOCUMENTS

| | | | |
|---|---|---|---|
| 5,029,332 | * | 7/1991 | Nakazawa . |
| 5,276,532 | * | 1/1994 | Harrington . |
| 5,600,574 | * | 2/1997 | Reitan . |
| 5,675,624 | * | 10/1997 | Relihan et al. . |
| 5,715,334 | * | 2/1998 | Peters . |

OTHER PUBLICATIONS

Lindley, C., Wiley Professional Computing—Practical Image Processing in C, John Wiley & Sons, Inc. (1991) (complete book).

* cited by examiner

Primary Examiner—David P. Porta
Assistant Examiner—Pamela R. Hobden
(74) Attorney, Agent, or Firm—Fenwick & West LLP (57) ABSTRACT

A digital x-ray image (600) is divided (802) into regions (602), (604) according to a selected (800) exposure compensation profile. Each region (602),(604) includes pixel values indicative of gray-scale levels in that region. The pixel values are used to index entries in one of a plurality of spatial LUTs (312a–n) assigned (804) to that region. Entries in the selected spatial LUT (312a–n) contain new pixel values indicative of a transform (806) on the original pixel values used to index the spatial LUT (312a–n). Original pixel values are replaced (808) with corresponding pixel values from the spatial LUT (312a–n). Each region of the x-ray image (600) needing compensation is transformed (806), in turn, until the entire image (600) is processed.

8 Claims, 8 Drawing Sheets

EXPOSURE COMPENSATION PROFILE

|  | BEGIN | END | LUT NO. |
|---|---|---|---|
| REGION NO. 1 | 0 | 32,768 | 1 |
| REGION NO. 2 | 32,769 | 65,536 | 2 |
| ⋮ | ⋮ | ⋮ | |
| REGION NO. N | | | |

EXPOSURE COMPENSATION FOR DIGITAL RADIOGRAPHY SYSTEMS USING SPATIAL LOOK-UP TABLES

RELATED APPLICATIONS

The subject matter of this application is related to U.S. patent application Ser. No. 09/153,937, entitled "Exposure Control For Digital Radiography Systems Using Charge Build-up in Sensor Array Pixels," filed on Sep. 16, 1998, by Harry Garland and Gerald May, which is incorporated by reference herein in its entirety.

The subject matter of this application is also related to U.S. patent application Ser. No. 09/154,534, entitled "Exposure Compensation For Digital Radiography Systems Using Selective Scanning Of Sensor Arrays," filed on Sep. 16, 1998, by Harry Garland and Gerald May.

TECHNICAL FIELD

The invention relates to exposure compensation for digital radiography systems, and more particularly, to providing digital x-ray images having uniform optical density.

BACKGROUND ART

One of the most difficult tasks facing radiographers using conventional radiographic techniques (e.g., x-ray film) is producing a diagnostic image of uniform optical density when examining a body part that varies greatly in thickness or tissue composition. Conventional compensation techniques for density variation typically include a compensating filter. Compensating filters can be fabricated for many procedures, and therefore come in various sizes and shapes. They are usually constructed of aluminum or plastics.

One commonly used filter is a wedge filter. The wedge filter is used when exposing a body part, such as the human foot, to x-rays. For example, during examination of the foot, the wedge is positioned with its thick portion shadowing the toes and the thin portion toward the heel. The thick portion of the wedge absorbs excess radiation, thereby preventing overexposure of the toes. The thin portion of the wedge allows more radiation to penetrate the heel, thereby preventing underexposure of the heel. The overall benefit of using the wedge is to provide an image with uniform optical density.

Alternatively, wedge filters may be used to calibrate x-ray machines and evaluate radiography procedures. For example, when an object of varying thickness is x-rayed, a "step" wedge of the same material incorporating the same thickness variations can be used to determine sensitivity levels for each thickness. Step wedges comprise a continuous series of steps which can be manufactured to a customer's specifications for any height or width, step dimensions, total number of steps, and total height of step wedge. By placing, for example, a penetrameter on each step of the wedge and exposing the step wedge to x-rays, the sensitivity levels for each thickness of an object can be determined.

Other types of compensating filters are commonly used with x-ray procedures and/or systems. These include "trough" filters for examining the chest, "bow-tie" filters to compensate for the shape of the head or body, and "conic" filters (e.g., concave, convex) for use in digital fluoroscopy, where the image receptor and the imageintensifier tube are round.

Currently, digital radiography systems are beginning to replace conventional x-ray systems. Digital radiography systems provide high quality digital x-rays by capturing x-ray images with a sensor plate having a matrix or array of silicon detectors. The x-ray images can be transmitted to a diagnostic viewer or any other output device, or to any other location via, for example, an Ethernet interface.

The sensor plate provides several advantages over conventional x-ray film. For example, unlike conventional x-ray film, digital images can be previewed within a few seconds of x-ray exposure. Moreover, the sensor plate used in digital systems can capture most patient imaging areas with high resolution (e.g., 160×160 microns pixel size, with 4096 gray scale (12 bit) contrast). The sensor plate also covers a larger dynamic range than conventional x-ray film.

Like conventional x-ray film, digital radiography systems require exposure compensation for some procedures. It is desirable therefore to have a system and method for compensating exposure deficiencies in a digital radiography system. Such a system and method preferably is integrated with existing digital radiography systems and provides simple, low cost exposure compensation without resorting to conventional compensation filters.

SUMMARY OF THE INVENTION

A digital x-ray image (600) is divided (802) into regions (602), (604) according to a selected (800) exposure compensation profile. Those regions (602), (604) needing compensation are assigned (804) to at least one of a plurality of spatial LUTs (312a–n). Each assigned region (602), (604) in the x-ray image (600) is transformed (806), in turn, by its assigned spatial LUT (312a–n) until the entire x-ray image (600) is processed.

BRIEF DESCRIPTION OF THE DRAWINGS

These and other more detailed and specific objects and features of the present invention are more fully disclosed in the following specification, reference being had to the accompanying drawings, in which.

DETAILED DESCRIPTION OF THE PREFERRED EMBODIMENTS

Figure 1:
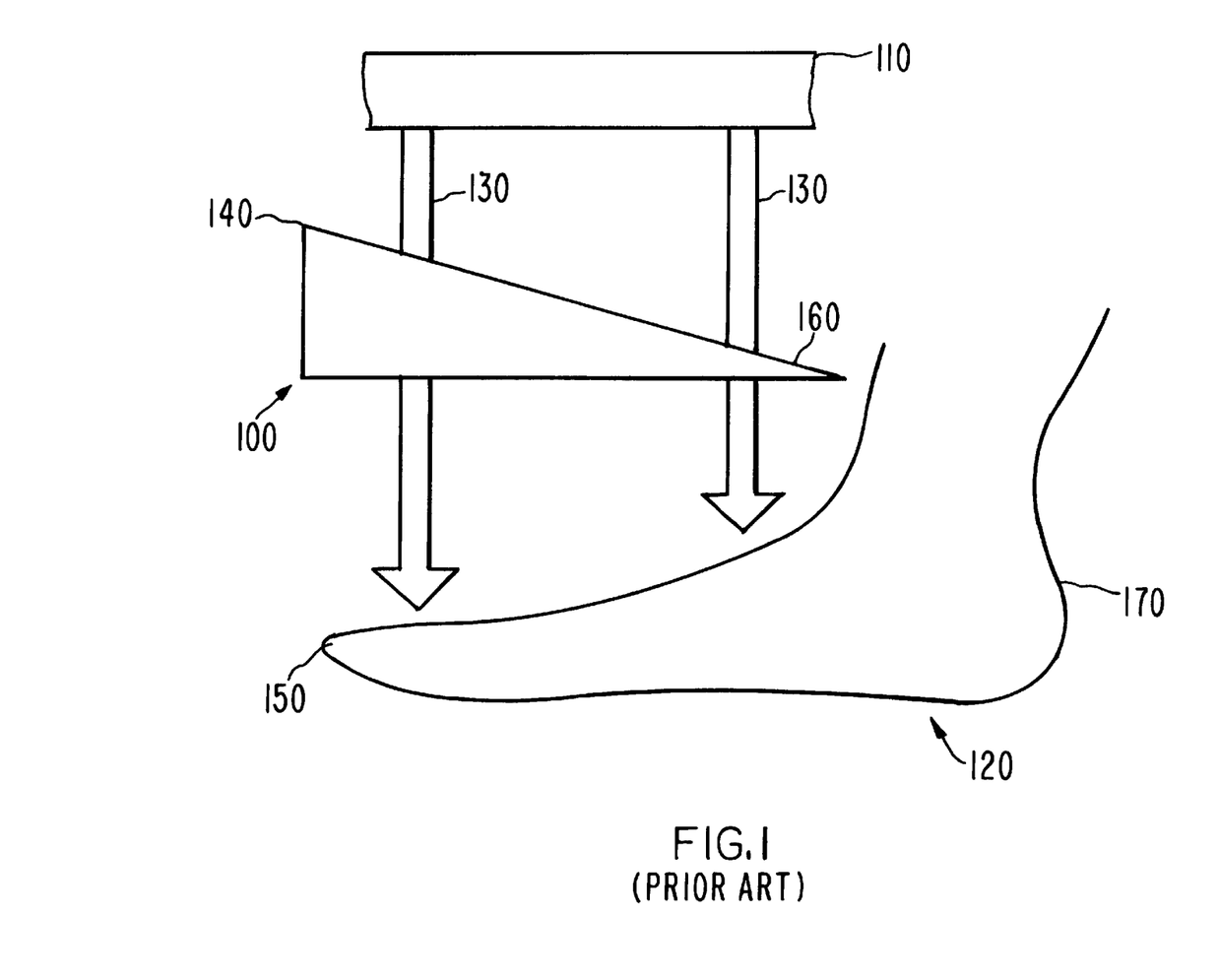
FIG. 1 is an illustration of a conventional wedge filter for compensating the exposure of a human foot to x-154 rays.

Referring to FIG. 1, there is shown an illustration of a conventional wedge filter 100 for compensating exposure of a human foot 120 to x-rays 130. The wedge filter 100 is positioned between an x-ray source 110 and the human foot 120. The wedge filter has a thick portion 140 and a thin portion 160. The thick portion 140 of the wedge filter 100 is positioned over the toes 150 of the foot 120, and the thin portion 160 of the wedge filter 100 is positioned toward the heel 170 of the foot 120. The wedge filter 100 typically is made of metal or plastic.

During examination, x-rays 130 generated by the x-ray source 110 are directed toward the human foot 120. The x-rays 130 penetrate through the foot 120 and impinge a sheet of x-ray film (not shown) disposed on the opposite side of the foot 120. The thick portion 140 of the wedge filter 100 absorbs a portion of x-rays 130 before they penetrate the toes 150, thereby preventing their overexposure. In contrast, the thin portion 160 of the wedge filter 100 allows more x-rays 130 to penetrate the heel 170, thereby preventing its underexposure.

A benefit of using the wedge filter 100 is to provide x-ray images with uniform optical density, thereby making such images suitable for diagnostic purposes. The wedge filter 100 is a useful tool for certain procedures using conventional x-ray film systems. Pre-fabricated filters, such as the wedge filter 100, however, can be inconvenient and difficult to use accurately. For example, the placement of a fabricated filter with respect to a particular anatomic region can be time consuming, thereby extending the duration of the examination of the patient who may be critically ill or experiencing discomfort.

While the wedge filter 100 and the human foot 120 are examples referred to throughout the specification in relation to x-ray exposure compensation, the present invention is applicable to other types of compensation as well. These include, for example, "trough" filters for examining the chest, "bow-tie" filters for use with CT to compensate for the shape of the head or body, and "conic" filters (e.g., concave, convex) for use in digital fluoroscopy, where the image receptor and the image-intensifier tube are round.

Figure 2A:
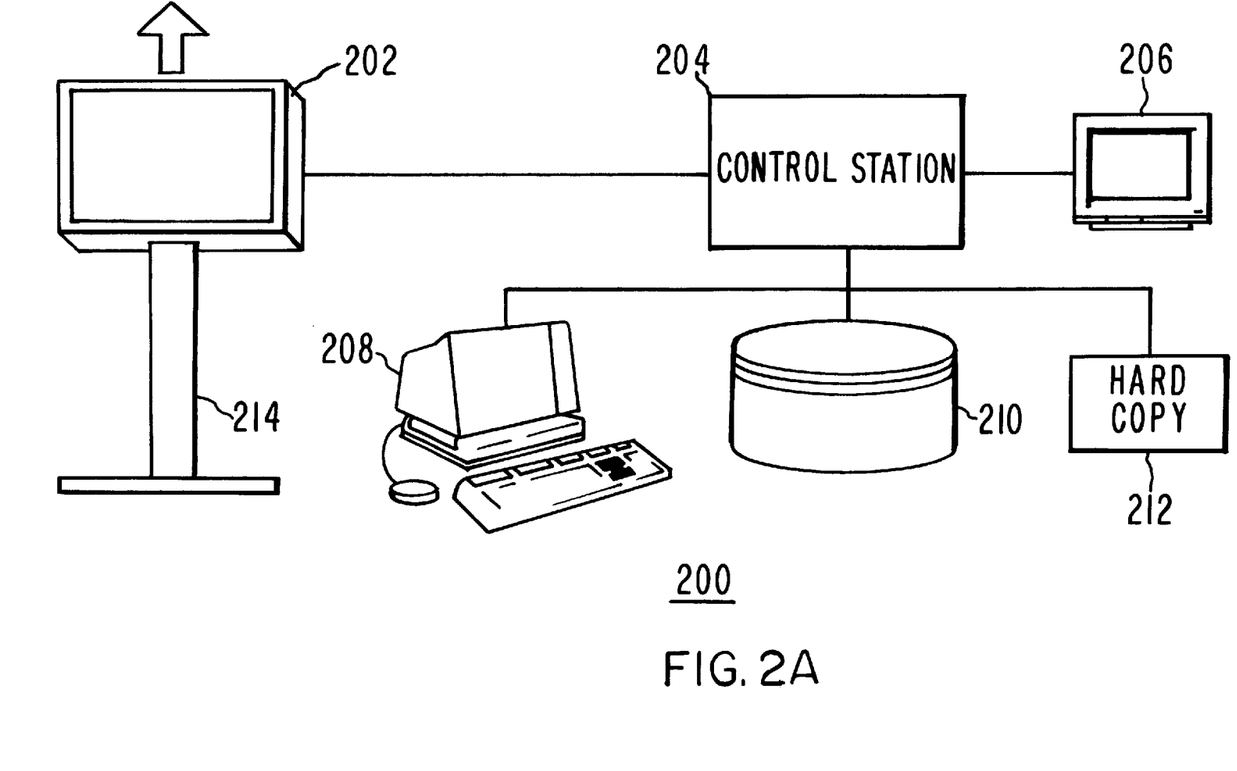
FIG. 2A is an illustration of one embodiment of a digital radiography system in accordance with the present invention.
Figure 2B:
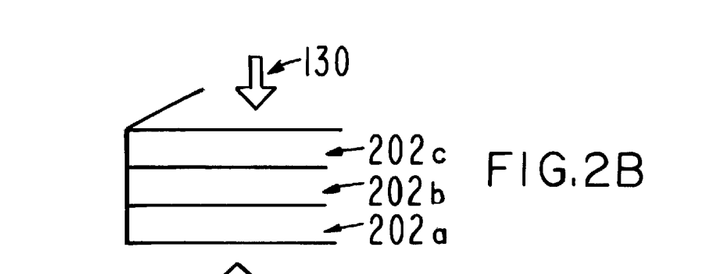
FIG. 2B is a sectional side view of the sensor unit 202 in FIG. 2A in accordance with the present invention.

Referring to FIG. 2A, there is shown a functional diagram illustrating one embodiment of a digital radiography system 200 in accordance with the present invention. The system 200 includes a sensor unit 202, a control station 204, an operation panel 206, a viewing workstation 208, an image archiver 210, and a hard copy output device 212. The sensor unit 202 is mounted on an upright stand 214 and coupled to the control station 204. A sectional side view of the sensor unit 202 in FIG. 2B shows three elements: a sensor plate 202a, a scintillator 202b, and a protective covering 202c. The sensor plate 202a includes a sensor array of pixels for capturing x-ray images. The term pixel (i.e., picture element), as used hereinafter, is the smallest part of an image that a computer printer or display can control. An image on a computer display can consist of hundreds of thousands of pixels, arranged in such a manner that they appear to be connected. For continuous-tone images, each pixel is assigned a numerical value (hereinafter also referred to as a "pixel value") that is directly mapped into a gray-scale palette and loaded in, for example, a video display adapter (VGA). The image can then be displayed in evenly spaced shades of gray.

The scintillator 202b is disposed on top of the sensor plate 202a to convert ionizing radiation from x-rays 130 into a visible light spectrum that the sensor plate 202a can detect. The protective covering 202c is disposed on the top of the scintillator 202b for protecting the sensor plate 202a from the environment.

The control station 204 is coupled to the sensor unit 202, the operation panel 206, the viewing workstation 208, the image archiver 210, and the hard copy output device 212. The control station 204 is for image processing and temporary storage of x-ray images.

The operation panel 206 is coupled to the control station 204 for primary image checking, data input of patient and exposure information, and selection of image processing.

The viewing workstation 208 is coupled to the control station 204, the image archiver 210, and the hard copy output device 212. The viewing workstation 208 is for assisting a radiologist in making a diagnosis based on x-ray images. The radiologist can view and compare new images with images stored in the image archiver 210. The viewing workstation 208 is also used to implement the present invention as described in detail below in conjunction with FIG. 3.

The image archiver 210 is coupled to the control station 204, the viewing workstation 208, and the hard copy output device 212. The image archiver 210 provides long term storage of x-ray images.

The hard copy output device 212 is coupled to the control station 204, the image archiver 210, and the viewing workstation 208. The hard copy output device 212 provides hard copies of x-ray images.

During a patient examination, a patient's body part is placed between the sensor unit 202 and an x-ray source (not shown). Using the operation panel 206, a radiographer inputs patient and exposure information, selects a desired image processing technique, and previews the x-ray image. The body part is then exposed to x-rays from the x-ray source. The x-rays penetrate the body part and ultimately impinge the pixels disposed on the sensor plate. The pixels transform the x-ray energy into photocurrent which can be summed, for example, by an integrating amplifier, over a predetermined exposure time. This photocurrent typically is proportional to the effective x-ray intensity on the pixel. Most human body parts are composed of organic matter such as fluid, bone, cartilage, and soft tissue, and each type of matter absorbs x-rays at a different rate. Therefore, over a predetermined exposure time the intensity of x-rays across the sensor array will vary due to these absorption rates. This intensity can be quantified and assigned a numerical value indicative of a gray-scale which can be used by a computer to construct a continuous-tone x-ray image suitable for diagnostic purposes as described in detail below.

After the x-ray image is captured by the sensor unit 202, it can be transferred to one or more devices such as the viewing workstation 208, the image archiver 210, and the hard copy output device 212. These devices can assist the radiologist in her diagnosis of the patient.

The digital radiography system described above provides several advantages over conventional film systems. For example, it is much quicker to get an image using a digital radiography system. An image can be acquired in about six seconds. The image can be quickly previewed to determine if the correct exposure time was used. With conventional film systems, it takes several minutes for the film to develop. During this time, the doctor cannot release the patient until she is certain the x-ray was properly taken, thereby subjecting the patient to inconvenience and discomfort for an extended period of time.

Also, with a digital system a radiographer can apply image processing techniques after the image has been captured. The digital images can be stored in long-term archive and recalled at will for a comparative diagnosis. This is not true for film-based systems, where exposed film is stored off-site, thereby making it difficult to retrieve for comparative diagnosis.

Another advantage associated with digital systems is its large dynamic range. While film-based systems probably provide better spatial resolution than digital systems, in most cases the greater dynamic range of the sensor plates will typically outweigh any loss in spatial resolution.

Figure 3:
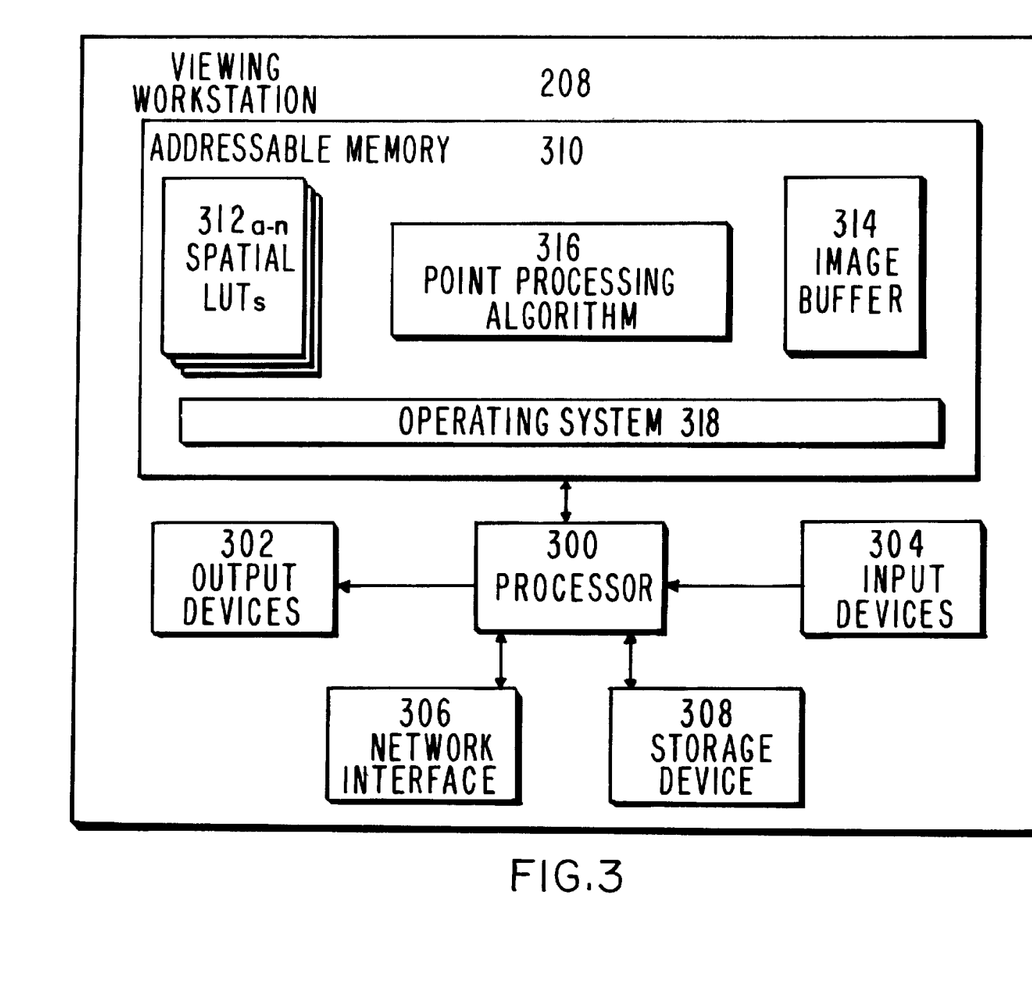
FIG. 3 is a block diagram of one embodiment of the viewing workstation 208 in FIG. 2 in accordance with the present invention.

Referring to FIG. 3, there is shown a functional block diagram of one embodiment of the viewing workstation 208 in FIG. 2 in accordance with the present invention. The viewing workstation 208 includes a processor 300, output devices 302, input devices 304, a network interface 306, a storage device 308, and addressable memory 310. These devices can be coupled together via a conventional computer data bus such as Peripheral Component Interconnect (PCI), Small Computer System Interface (SCSI), or Extended Industry Standard Architecture (EISA).

The processor 300 can be, for example, a Pentium® II processor manufactured by Intel, Inc. of Santa Clara, Calif. The output devices 302 include, for example, a computer display and/or the hard copy output device 212 (e.g., printer). The input devices 304 can be, for example, a mouse, track-ball, keyboard, or any other control device for allowing a user to interact with the viewing workstation 208. The storage device 308 can be the image archiver 210, or any other hard disk or optical device for storing digital information and data. The network interface 306 is, for example, an Ethernet interface for communicating with, for example, a Local Area Network (LAN).

The addressable memory 310 includes, a plurality of spatial LUTs 312a–n, where n is the total number of spatial LUTs. The addressable memory 310 also includes an image buffer 314, a point processing algorithm 316, and an operating system 318. The addressable memory 310 can be, for example, Random Access Memory (RAM), Read-only Memory (ROM), or any other memory device. The operating system 318 can be, for example, Windows® '95 made by Microsoft Corporation of Redmond, Wash. The operating system 318, along with conventional device drivers (not shown), handles most of the basic functions of the viewing workstation 208 including communication with peripherals.

In the preferred embodiment, digital x-ray images are captured by the sensor unit 202 and transferred to the viewing station 208 via the network shown in FIG. 2. Upon arrival, the digital image is stored in the image buffer 314 a located in addressable memory 310. The image buffer 314 can be either static or dynamically allocated during runtime. In the preferred embodiment, a block of addressable memory 310 is dynamically allocated as the image buffer 314. Each pixel in the image buffer 314 can be manipulated (e.g., identified, changed) using known programming techniques for array indexing.

After storing the x-ray image in the image buffer 314, the radiographer determines whether the image needs exposure compensation based on visual inspection of the x-ray's optical density. If exposure compensation is needed, the radiographer can select an appropriate exposure compensation profile from a database of profiles (not shown). These profiles contain, in part, computer readable instructions on how to divide the x-ray image into regions and which spatial LUTs 312a–n to assign to the regions. The profiles can be derived empirically for a variety of x-ray procedures, anatomic regions, and view angles, as described below.

After selecting a compensation profile, the point processing algorithm 316 takes the pixel values from a specified region of the image buffer 314 and uses these pixel values to index entries in an assigned one of the spatial LUTs 312a–n. Each entry of the assigned one of LUTs 312a–n contains a new pixel value indicative of a transform on the original pixel value used to index such entry. In the preferred embodiment, this transform provides an image having relatively uniform optical density. Alternatively, the spatial LUTs 312a–n can be implemented in hardware. In a hardware implementation, a pixel's value can be used as an address into RAM, causing the RAM content, i.e., new pixel values, to be returned. Although hardware implementations of LUTs usually provide fast processing, they are expensive to implement.

Figure 4:
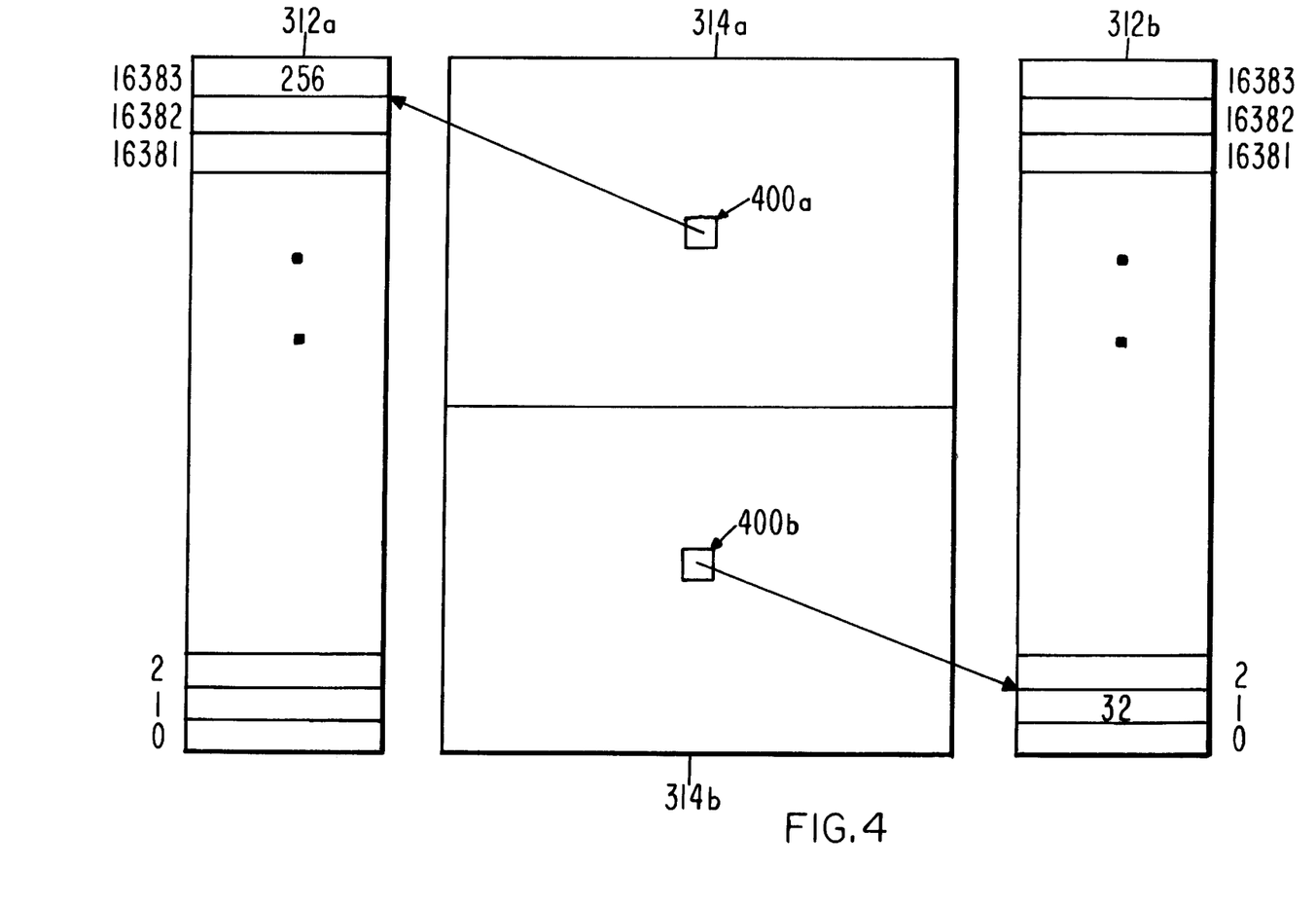
FIG. 4 is an illustration of spatial LUTs for use with the viewing workstation 208 in FIG. 2 to compensate digital x-rays for exposure problems in accordance with the present invention.

Referring to FIG. 4, there is shown an illustration of one embodiment of spatial LUTs 312a–n for use with the viewing workstation 208 in FIG. 2 in accordance with the present invention. The image buffer 314 includes an image array (not shown) for storing pixel values. In the preferred embodiment, the pixel values range from 0 to 16383, which is 14 bits/pixel. Each pixel value represents one of 16383 shades of gray in a 14-bit gray-scale palette. Based on a selected compensation profile, the image buffer 314 is divided into region 314a and region 314b. Region 314a is assigned spatial LUT 312a. Region 314b is assigned spatial LUT 312b. For illustrative purposes, regions 314a and 314b each includes an exemplary pixel value 400a and 400b, respectively.

As shown in FIG. 4, the pixel value 400a is 16383. This number represents an upper boundary on the range of possible gray-scale levels. The gray-scale level 16383 can be indicative of black or white in the gray-scale palette. The point processing algorithm 316 uses the pixel value 16383 to index the spatial LUT 312a at entry 16383. The new pixel value contained in entry 16383 is, for example, the pixel value 256. The pixel value 256 is used by the point processing algorithm 316 to replace the original pixel value 400a in region 314a of the image array. This procedure is repeated until each pixel value in region 314a is replaced with a new pixel value from the corresponding entry of the spatial LUT 312a. Similarly, the pixel value 400b is originally set equal to 1. This value is indicative of a particular shade of gray. The point processing algorithm 316 uses the pixel value 1 to index the spatial LUT 312b at entry 1. The new pixel value contained in entry 1 of the spatial LUT 312b is, for example, the pixel value 32. The pixel value 32 is used by the point processing algorithm 316 to replace the original pixel value 400b in region 314b of the image array. This procedure is repeated until each pixel value in region 314b is replaced with a new pixel value from the spatial LUT 312b.

Figure 5A:
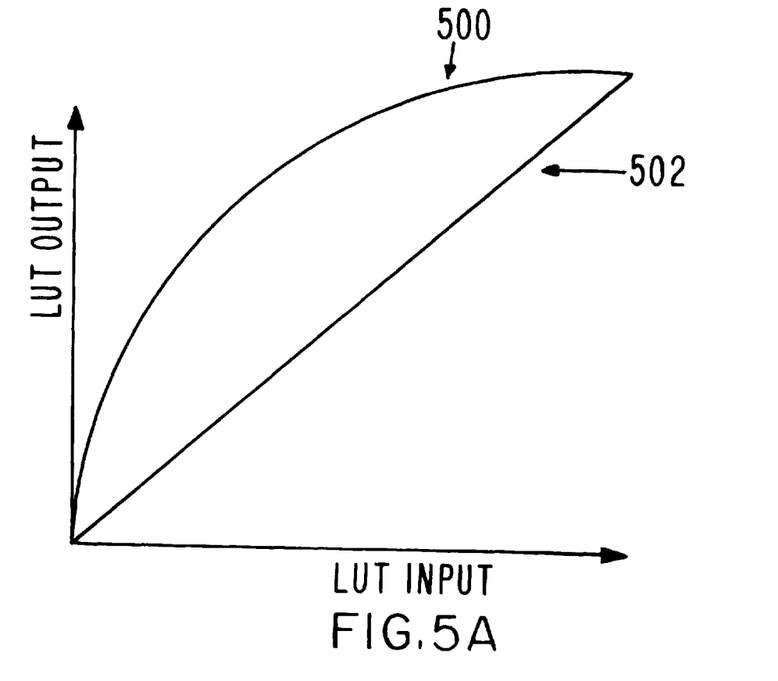
FIGS. 5A and 5B are graphs illustrating the use of spatial LUTs to lighten and darken regions in digital x-ray images in accordance with the present invention.
Figure 5B:
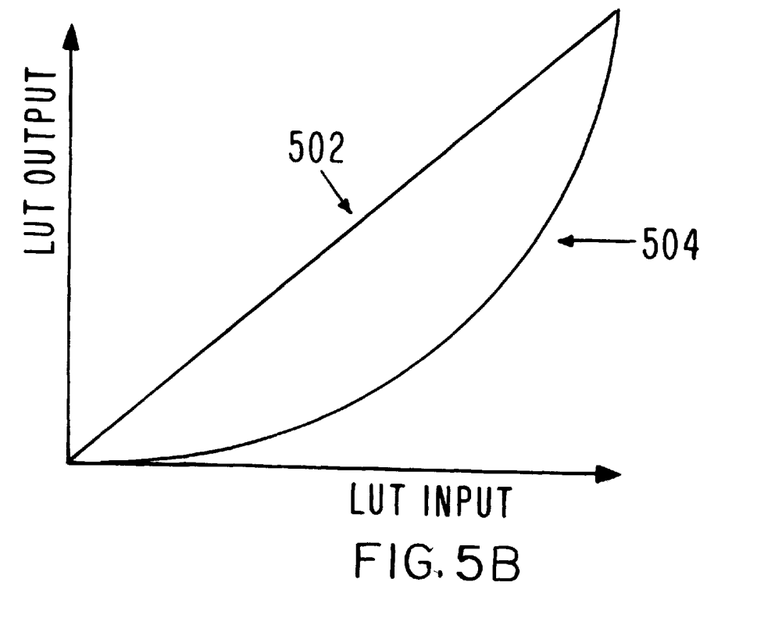

Referring to FIGS. 5A and 5B, there is shown graphs illustrating the use of spatial LUTs to lighten and darken regions in a digital x-ray image in accordance with the present invention. The horizontal axes of the graphs represent the original pixel values for indexing spatial LUTs 312. The vertical axis represents the new pixel values used to replace the original pixel values in the image buffer 314 as described above in conjunction with FIG. 4.

Curve 502 in FIGS. 5A and 5B represents a linear transformation on the original pixel values. In other words, a pixel value of 0 will be replaced with a pixel value of 0, and a pixel value of 1 will be replaced with a pixel value of 1, and so on. By contrast, curves 500 and 504 will transform the original pixel values to lighter and darker values, respectively, assuming that the higher the input pixel value the lighter the shade of gray.

The functions represented by curves 502 and 504 can be implemented using classical image processing techniques that make use of histograms to determine whether an image has a uniform optical density. A histogram is a graph of the distribution of pixel-intensity values for an image or portion of an image. For example, low contrast x-ray images are composed of a limited range of tones or shades of gray. These images are usually too light or too dark to the human eye due to overexposure and underexposure, respectively. On a histogram this condition is detectable when all the pixel values are clustered together and occupy only a small portion of the possible pixel value range. In the preferred embodiment, histograms are used in conjunction with contrast stretching techniques to increase the contrast of x-ray images, as described in Craig A. Lindley, *Practical Image Processing In C* (1991; John Wiley & Sons, Inc., NY), incorporated by reference herein in its entirety.

Figure 6:
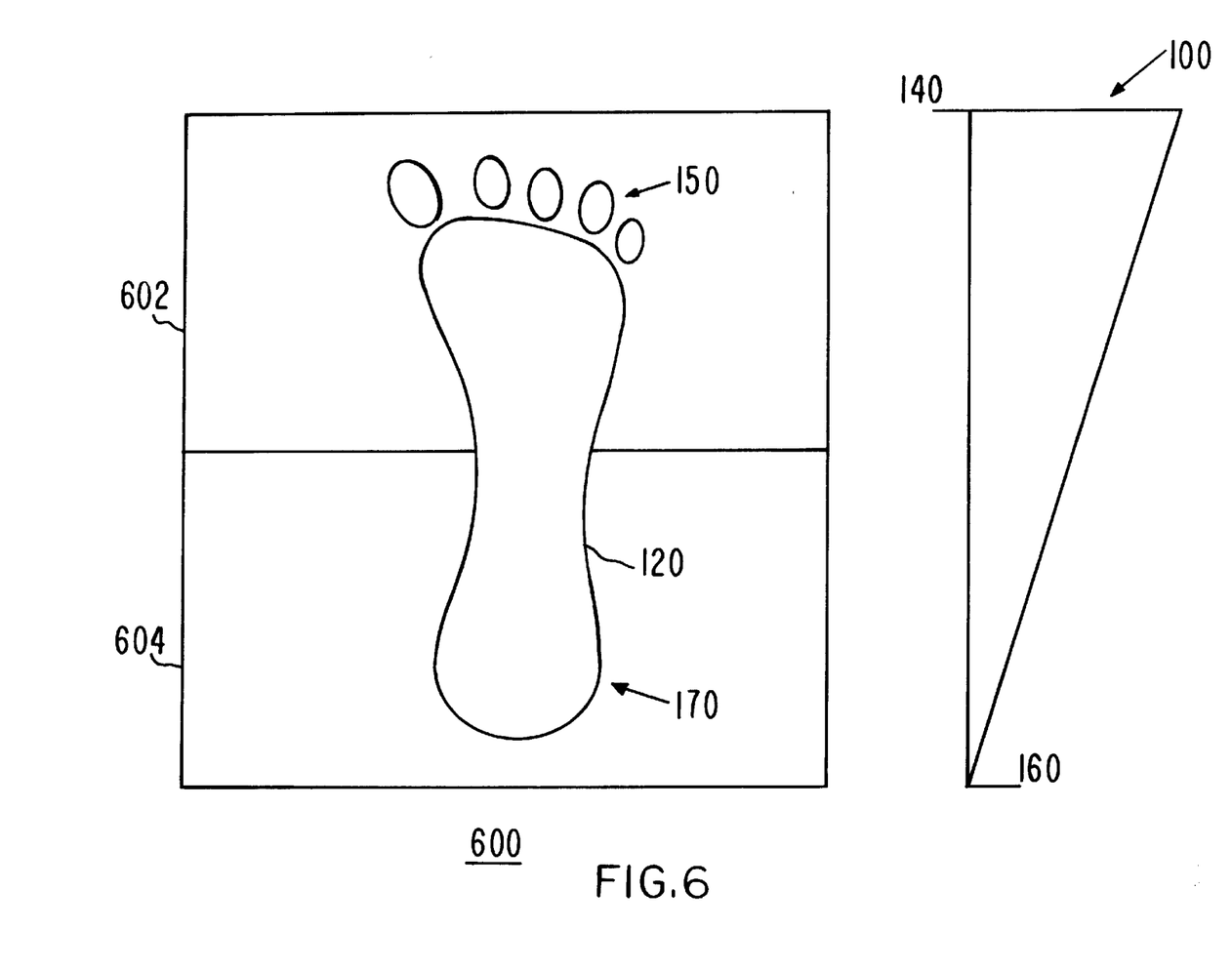
FIG. 6 is an illustration of exposure compensation of the human foot 120 using spatial LUTs that emulate the wedge filter 100 in FIG. 1 in accordance with the present invention.

Referring to FIG. 6, there is an illustration of spatial LUTs for use in emulating the wedge filter 100 in FIG. 1 in accordance with the present invention. An x-ray image 600 is taken of a human foot 120. The human foot has toes 150 and a heel 170. The toes 50 lie in the upper half region of the image 600 and the heel lies in the lower half region of the image 600. An outline of a conventional wedge filter 100 is disposed next to the x-ray image 600 for illustrative purposes only. The wedge filter 100 has a thick portion 140 and a thin portion 160.

The present invention uses spatial LUTs to emulate the wedge filter 100, which is commonly used to compensate for overexposure of the toes 150 and underexposure of the heel 170 to x-rays. In the preferred embodiment, a cycle of operation begins when the radiographer selects an exposure compensation profile from a database. Here, the exposure compensation profile emulates the wedge filter 100 for examination of a human foot 120. Based on this profile, the x-ray image 600 is divided into an upper region 602 and a lower region 604. The upper region 602 is transformed by spatial LUT 312a and the lower region 604 is transformed by spatial LUT 312b. These transformations are implemented using the point processing algorithm 316 shown in FIG. 3. The spatial LUT 312a contains pixel values that implement curve 504 in FIG. 5B. That is, the overexposed region 602 is darkened. Similarly, the spatial LUT 312b contains pixel values that implement curve 500 in FIG. 5A. That is, the underexposed region 604 is lightened. As stated previously, the curves 502 and 504 can be implemented with conventional histograms and contrast stretching to help maintain a relatively uniform optical density across the entire x-ray image 600.

It is noted that curves 500 and 504 are just two examples of the type of exposure compensation that can be achieved with the present invention. The type of exposure compensation needed depends on several factors including the tissue density variation of the body part, view angle, and x-ray procedure. For example, other types of compensating filters commonly used with x-ray procedures can be emulated by the present invention. These include "trough" filters for examining the chest, "bow-tie" filters to compensate for the shape of the head or body, and "conic" filters (e.g., concave, convex) for use in digital fluoroscopy, where the image receptor and the image-intensifier tube are round.

Figure 7:
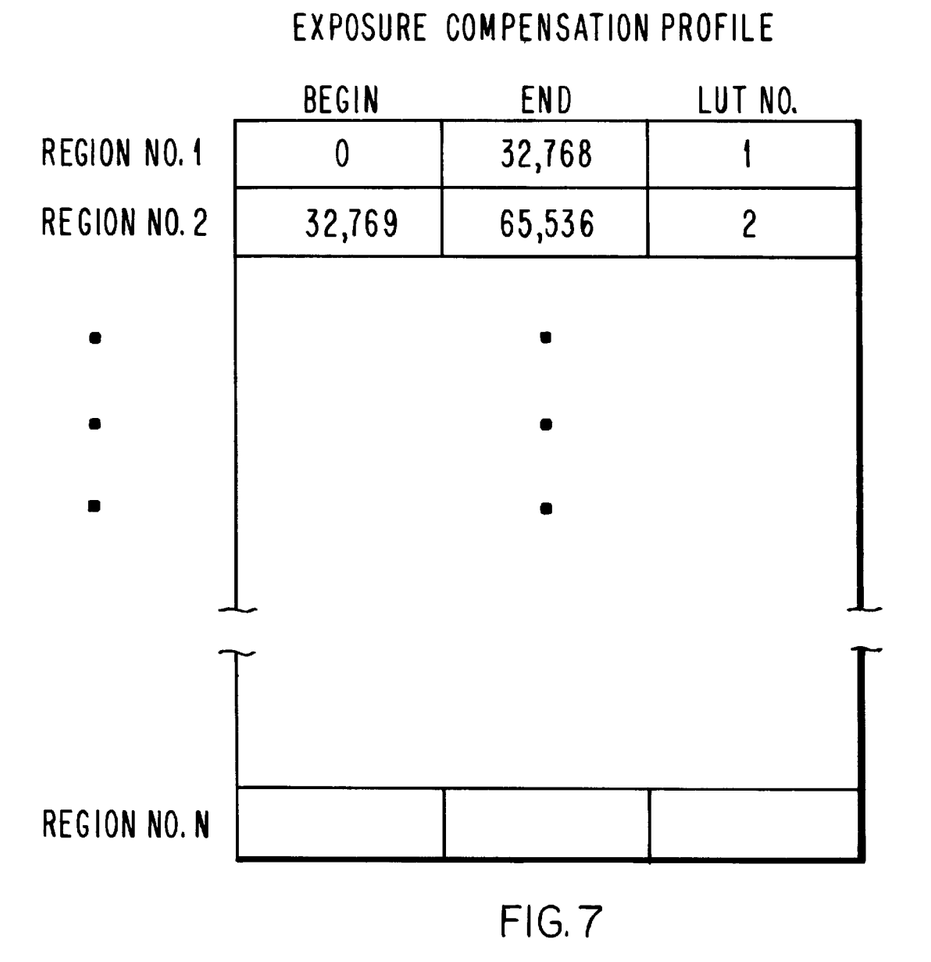
FIG. 7 is an illustration of one embodiment of an exposure compensation profile in accordance with the present invention.

Referring to FIG. 7, there is shown an illustration of one embodiment of an exposure compensation profile in accordance with the present invention. The exposure compensation profile can be generated during patient examination using, in part, low dose exposure techniques as disclosed in U.S. patent application Ser. No. 09/153,937 entitled "Exposure Control For Digital Radiography Systems Using Charge Build-up in Sensor Array Pixels," filed on Sep. 16, 1998, by Harry Garland and Gerald May, which is incorporated by reference herein in its entirety.

In the preferred embodiment, the exposure compensation profile is a computer-readable file generated off-line and stored in a database. The profile preferably includes three fields designated BEGIN, END, and LUT No. The BEGIN and END fields delineate regions in an image array of pixel values. The image array is created in the image buffer 314 by processor 300 (FIG. 3). For example, a 256×256 image contains 65,536 pixels. Each pixel is associated with a pixel value which is stored in the image array in a one-toone correspondence. The image array can be divided into two regions as shown in FIG. 6. The first region has a BEGIN value of 0 and an End value of 32,768. The second region has a BEGIN value of 32,769 and an END value of 65,536. Thus, each region in the image array is delineated by a BEGIN value and an END value. These values can be used to extract a region of pixel values from the image array for processing. Once extracted, the region is processed by an assigned spatial LUT. The particular spatial LUT used is determined by the LUT No. located in the third field of the exposure compensation profile, as shown in FIG. 7. Each spatial LUT is assigned a unique number, for example, Region No. 1 is assigned to LUT No. 1. An x-ray image can be divided into N regions, where each region contains an arbitrary number of contiguous pixels. Each region of the x-ray image can be processed in the order that it appears in the exposure compensation profile.

Figure 8:
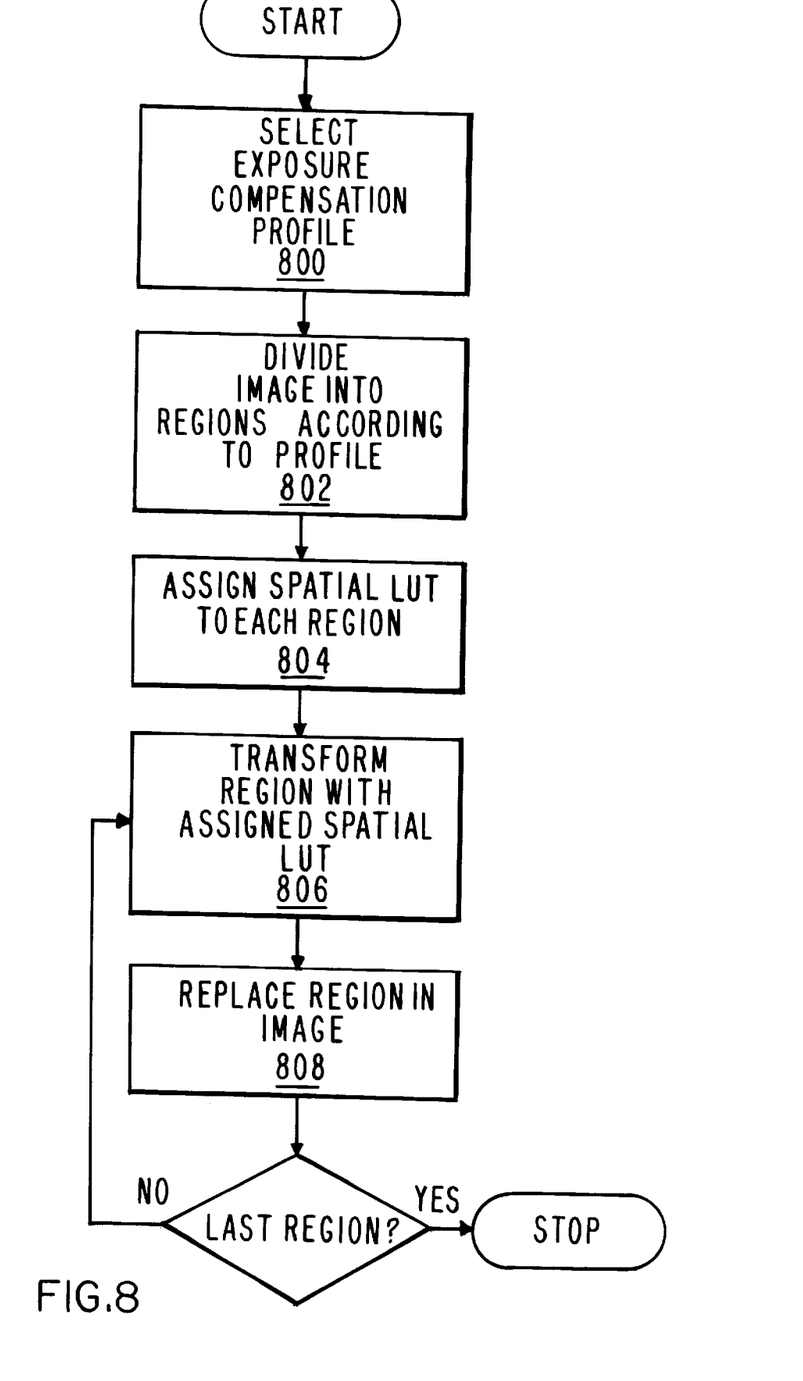
FIG. 8 is a functional flow diagram of an exposure compensation method using spatial look-up tables in accordance with the present invention.

Referring to FIG. 8, there is shown a functional flow diagram of an exposure compensation method using spatial look-up tables in accordance with the present invention. The method begins with the exposure compensation profile being selected 800 by the radiographer. Based on this selected profile, the image array containing the x-ray image is divided 802 into two or more regions as described in conjunction with FIG. 7. Each region is then assigned 804 to a spatial LUT according to the exposure compensation profile. Once a spatial LUT is assigned 804 to the region, each pixel value in that region is transformed 806 by the assigned spatial LUT in accordance with the selected profile. Each pixel value in the image array is replaced 808 with new pixel values contained in corresponding entries in the LUT. The method just described continues until the last region in the image array is transformed 806.

An advantage of the above method is each region in the x-ray image is independently compensated without effecting the compensation of other regions. The amount and type of compensation is determined by profiles, which are tailored for a particular x-ray procedure and/or view angle.

The above description is included to illustrate the operation of the preferred embodiments and is not meant to limit the scope of the present invention. The scope of the present invention is to be limited only by the following claims. From the above discussion, many variations will be apparent to one skilled in the art that would yet be encompassed by the spirit and scope of the present invention.

What is claimed is:

1. A method of compensating for x-ray exposure of a patient body part by a x-ray system, said x-ray system having a sensor array for capturing an x-ray image, said method comprising the steps of:

selecting an exposure compensation profile;

dividing the x-ray image into a plurality of regions according to said selected profile, said regions including first pixel values;

assigning compensation information containing second pixel values to a region according to said profile; and replacing said first pixel values with said second pixel values to compensate said region for x-ray overexposure or underexposure.

2. The method of claim 1, wherein said replacing step includes indexing an entry in a spatial look-up table using said first pixel value as an index, said first pixel value indicative of said entry in said spatial look-up table.

3. The method of claim 1, wherein said exposure compensation profile is used to emulate one from the group of conventional compensating filters consisting of a "wedge" filter, a "trough" filter, a "bow-tie" filter, and a "conic" filter.

4. A computer-readable medium having stored thereon instructions which, when executed by a processor, cause the processor to perform the steps of:

selecting an exposure compensation profile;

dividing an x-ray image into a plurality of regions according to said selected profile, said regions including first pixel values;

assigning compensation information containing second pixel values to a region according to said profile; and replacing said first pixel values with said second pixel values to compensate said region for x-ray overexposure or underexposure.

5. The computer-readable memory of claim 4, wherein said replacing step includes indexing an entry in a spatial look-up table using said first pixel value as an index, said first pixel value indicative of said entry in said spatial look-up table.

6. The computer-readable memory of claim 4, wherein said exposure compensation profile is used to emulate one from the group of conventional compensating filters consisting of a "wedge" filter, a "trough" filter, a "bow-tie" filter, and a "conic" filter.

7. The method of claim 1, wherein said assigning step includes assigning at least one spatial look-up table to each region according to said profile, said spatial look-up tables having entries corresponding to said first pixel values, said entries containing second pixel values.

8. The method of claim 4, wherein said assigning step includes assigning at least one spatial look-up table to each region according to said profile, said spatial look-up tables having entries corresponding to said first pixel values, said entries containing second pixel values.

* * * * *